United States Patent [19]

Steer

[11] Patent Number: 4,950,261
[45] Date of Patent: Aug. 21, 1990

[54] OSTOMY COUPLING

[75] Inventor: Peter L. Steer, Surrey, England

[73] Assignee: E. R. Squibb & Sons, Inc., Princeton, N.J.

[21] Appl. No.: 150,610

[22] Filed: Feb. 1, 1988

[51] Int. Cl.⁵ .............................................. A61F 5/44
[52] U.S. Cl. .................................................... 604/339
[58] Field of Search ............................... 604/332–345, 604/277

[56] References Cited

FOREIGN PATENT DOCUMENTS

| 3417183 | 11/1985 | Fed. Rep. of Germany ...... 604/337 |
| 2119654 | 11/1983 | United Kingdom . |
| 2115288 | 10/1984 | United Kingdom . |
| 2121902 | 7/1985 | United Kingdom . |
| 2183481 | 6/1987 | United Kingdom . |
| 21834181 | 6/1987 | United Kingdom . |
| 2148716 | 9/1987 | United Kingdom . |
| 2179556 | 9/1987 | United Kingdom . |
| 2193097 | 2/1988 | United Kingdom . |
| 2193893 | 2/1988 | United Kingdom . |

Primary Examiner—Jerome L. Kruter
Attorney, Agent, or Firm—Stephen B. Davis

[57] ABSTRACT

An ostomy coupling has a pair of coupling rings. The body side ring has a flange attached to a medical grade adhesive pad and a chute wall surrounding a stomal aperture. The bag side ring has a rib member and a seal strip. To provide easy disengagement, the bag side ring has an integral flexible latching arm having a hook portion positioned to engage under a hook flange on the body side ring when the rings are coupled. The hook portion is disengagable from the hook flange by a lifting movement of the latching arm.

7 Claims, 4 Drawing Sheets

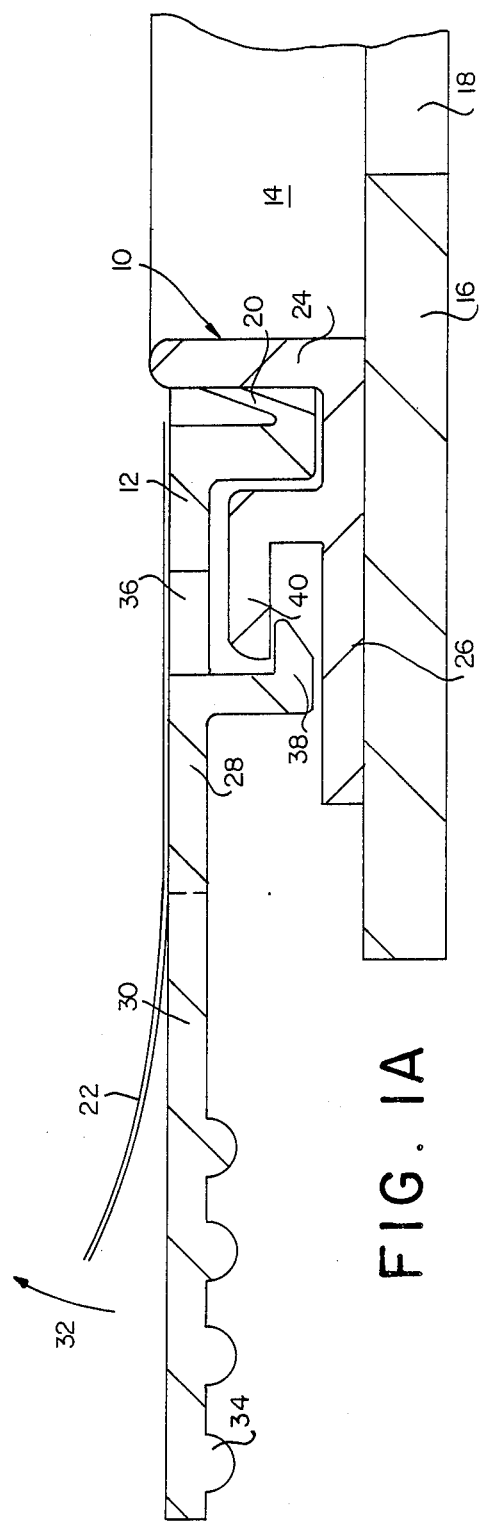
FIG. IA

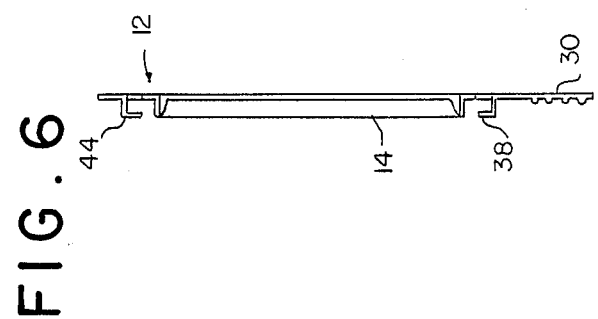
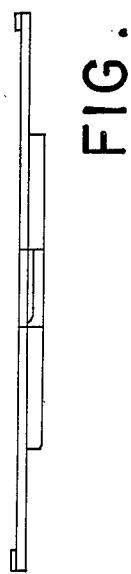
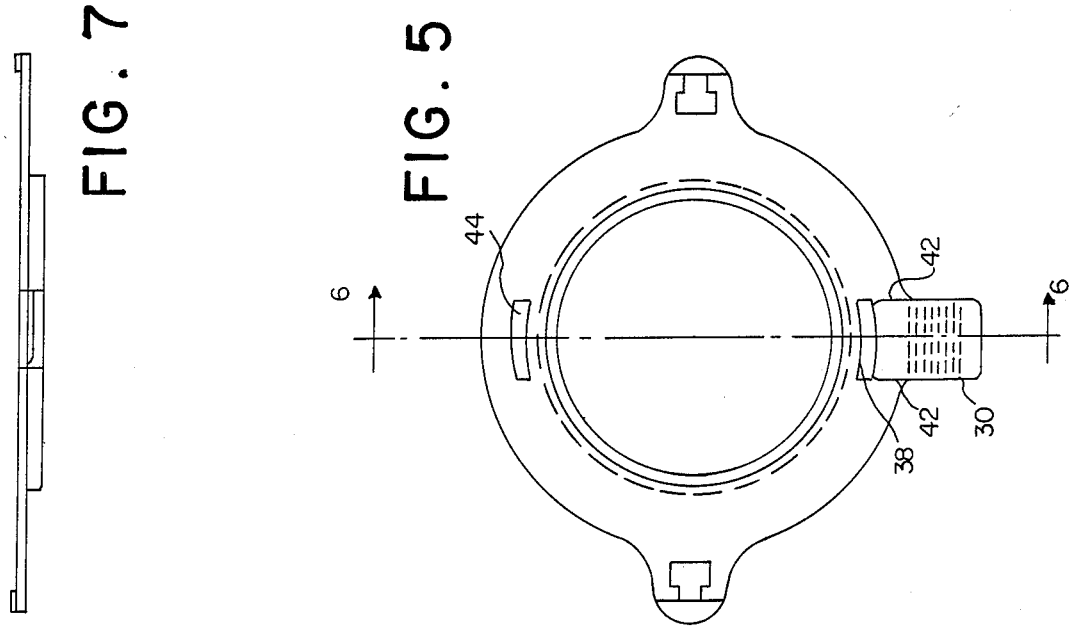

OSTOMY COUPLING

BACKGROUND OF THE INVENTION

The present invention relates to an ostomy coupling comprising a pair of coupling rings.

Ostomy couplings comprising a pair of coupling rings are known, and one commercially successful coupling of this kind is described and claimed in U.K. patent No. 1 571 657. Other British Patents of interest are Nos. 1 568 860, 1 586 823, and 1 586 824.

The present invention aims at providing an ostomy coupling having improved security of connection between the coupling rings and which yet can be readily manipulated to separate the coupling rings. Separation of the coupling rings is necessary in order to change a used bag for a new bag.

SUMMARY OF THE INVENTION

According to the present invention, an ostomy coupling comprises a pair of coupling rings of which the body side ring has a radially extending flange attachable to a pad of medical grade adhesive and a chute wall surrounding a stomal aperture, and the bag side ring has a rib member integral with a seal strip, the rib member being received by a channel portion of the body side ring when the rings are coupled together, and is characterised in that the bag side ring has an integral flexible latching arm having a hook portion positioned to engage under a hook flange on the body side ring when the rings are coupled, the hook portion being disengageable from the hook flange by a lifting movement of the arm.

BRIEF DESCRIPTION OF THE DRAWINGS

The invention will be better understood from the following description, given way of example only, of an illustrative embodiment of the invention. This description is given with reference to the accompanying drawings in which:

FIGS. 1A and 1B are a greatly enlarged axial cross-section through one example of coupling according to the invention, showing the body-side ring and the bag-side ring in their mutually connected condition;

FIG. 5 is a front view on a reduced scale of a bag side coupling ring;

FIG. 6 is an axial cross-section through the bag side coupling ring shown in FIG. 5, taken along the lines and arrows 6—6; and FIG. 7 is a side view of the bag side coupling of FIG. 5 taken along the lines and arrows 7—7 in FIG. 5.

DETAILED DESCRIPTION OF THE DRAWINGS

Figure 1B:
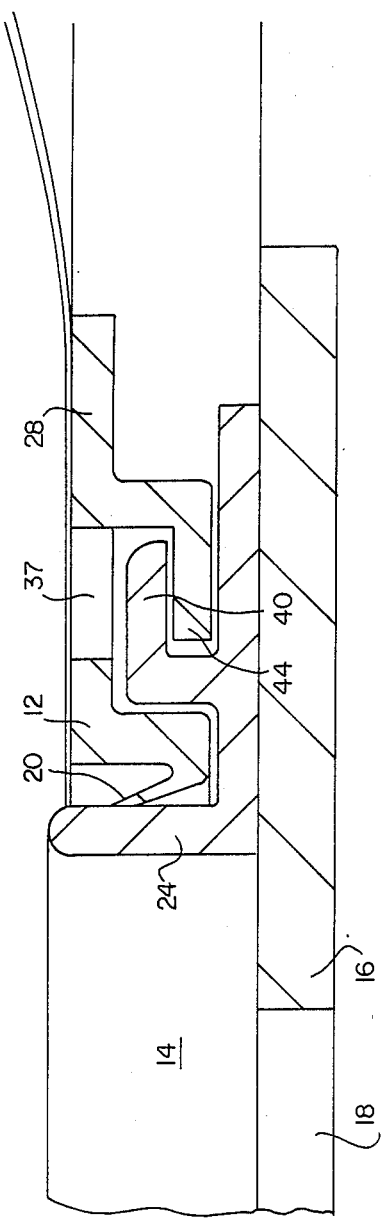
Figure 3:
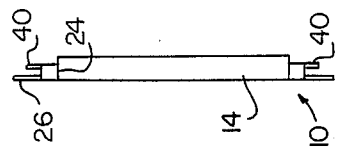
FIG. 3 is an axial cross-section through the body side coupling ring shown in FIG. 2, taken along the lines and arrows 3—3.
Figure 4:
FIG. 4 is a side view of the body side coupling of FIG. 2 taken along the lines and arrows 4—4 in FIG. 2.
Figure 2:
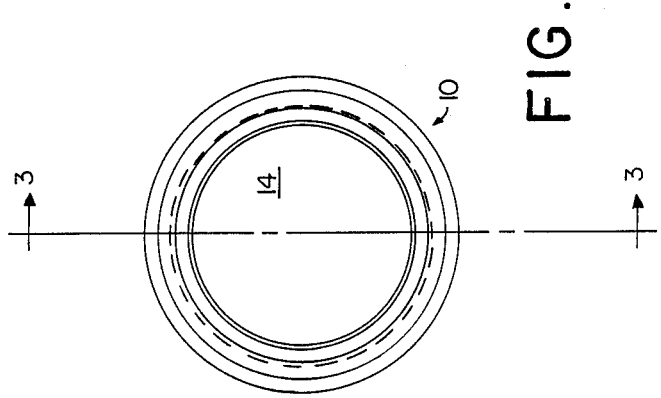
FIG. 2 is a front view on a reduced scale of a body-side coupling ring.

The body side coupling ring 10 includes a radially extending flange 26 which is attachable to a pad 16 of a medical grade adhesive. The body-side coupling ring 10 also has a cylindrical wall 24 surrounding the stomal aperture 14. This wall 24 serves as a chute to guide feacal discharges into an ostomy bag, one wall of which is seen at 22. The pad 16 has a stomal aperture 18 therein, and, as is conventional, the medical grade adhesive pad 16 is attached to the wearer over the peristomal skin surface.

The illustrated coupling also includes a bag-side ring 12 to which the ostomy bag 22 is secured in any convenient manner. The ring 12 has an internally projecting deflectable peripheral sealing strip 20 which, in use, engages the radially outer surface of the wall 24.

At one radial position on the bag side ring an integral flexible latching arm 30 joins the flange 28, this arm having a hook portion 38 positioned to engage under a hook flange 40 on the body-side ring 10, in order to couple the two coupling rings together. The hook flange 40 is formed integrally with the remainder of the body-side ring 10, and extends completely around the flange 26. On the other hand, the latching hook portion 38 is located at one peripheral position only, although, depending on the relative orientation of the two coupling rings when the coupling is assembled, the hook portion 38 may engage under the flange 40 at any peripheral postion. In other words, there is no necessity for the user when putting on a new bag, to adjust the rotary position of the bag side ring relative to the body side ring to any particular postion, because the continuous peripheral structure of the hook flange 40 means that the user can couple the bag-side ring at any relative rotational orientation between the two rings.

To facilitate manufacture by injection moulding techniques, the flange 28 has a slot 36 therein, substantially aligned with the latching hook portion 38, through which a removable moulding can be inserted and withdrawn during manufacture.

As an optional and not essential feature of the invention, the flexibility of the latching arm 30 relative to the remainder of the bag-side ring may be enhanced by the provision of relief slots through the flange 28. These slots may be located as shown at 42 on FIG. 5, but are not shown in any other Figure. In certain circumstances no such slots may be necessary. As seen best in FIGS. 1 and 5, a ridged or bumped formation may be employed for the latching arm, so that the user when he wishes to disengage the bag-side coupling part from the body-side coupling ring can conveniently pull the arm 30 in the direction indicated by the arrow 32, so causing the hook portion 38 to be disengaged so permitting the substitution of a clean bag.

On the body side ring, diametrically opposite to the latching arm 30, there is provided an integral flange 44 of limited peripheral extent. This flange 44 is made in one piece with the remainder of the bag-side coupling ring and an aperture 37 is provided to enable the flange 44 to be produced by injection moulding techniques. As seen best in the right hand side of FIG. 1, in the coupled position of the two coupling rings, the flanges 40 and 44 are interengaged. Once the latching arm 30 has been lifted and the left hand side of the engaged coupling rings (as seen in FIG. 1) have been separated, then by a lateral motion to the right the flange 44 on the bag-side ring can be disengaged from the body-side ring which is then still on the wearer.

As will be understood by one skilled in the art, the invention can be carried into effect in different ways. For example, while it is desirable that the hook flange 40 should extend completely around the body-side coupling, this is not essential. Other means of sealing than the flexible sealing strip 20 could be employed to effect a seal between the bag-side and body-side coupling rings. The invention is not regarded as limited to the details of the embodiment illustrated.

I claim:

1. An ostomy coupling comprising a pair of coupling rings of which the body side ring has a radially extending flange attachable to a pad of medical grade adhesive and a chute wall surrounding a stomal aperture, and the bag side ring has a rib member integral with a seal strip, the rib member being received by a channel portion of the body side ring when the rings are coupled together, said bag side ring including an integral flexible latching arm having a hook portion positioned to engage under a hook flange on the body side ring when the rings are coupled, said radially extending flange extending from said chute wall to under said hook portion the hook portion being disengageable from the hook flange by a lifting movement of the arm.

2. An ostomy coupling according to claim 1 in which the hook flange is peripherally continuous on the body side ring.

3. An ostomy coupling according to claim 2 in which the bag side member has a radially extending flange which has a slot therein, substantially aligned with the latching hook portion, through which slot a removable moulding tool can be inserted and withdrawn during manufacture.

4. An ostomy coupling according to claim 2 in which there are relief slots provided in the bag side ring to improve flexibility of the latching arm relative to the remainder of the bag side ring.

5. An ostomy coupling according to claim 1 in which the bag side member has a radially extending flange which has a slot therein, substantially aligned with the latching hook portion, through which slot a removable moulding tool can be inserted and withdrawn during manufacture.

6. An ostomy coupling according to claim 5 in which there are relief slots provided in the bag side ring to improve flexibility of the latching arm relative to the remainder of the bag side ring.

7. An ostomy coupling according to claim 1, in which there are relief slots provided in the bag side ring to improve flexibility of the latching arm relative to the remainder of the bag side ring.

* * * * *